United States Patent [19]

Peterson et al.

[11] 4,451,374
[45] May 29, 1984

[54] LIQUID CHROMATOGRAPHIC METHOD AND POST-COLUMN EFFLUENT TREATMENT FOR DETECTION AND SEPARATION AT OPTIMIZED PH

[75] Inventors: Dennis P. Peterson, Midland; James C. Davis, East Lansing, both of Mich.

[73] Assignee: The Dow Chemical Company, Midland, Mich.

[21] Appl. No.: 465,976

[22] Filed: Feb. 14, 1983

Related U.S. Application Data

[63] Continuation of Ser. No. 274,127, Jun. 16, 1981, abandoned, which is a continuation of Ser. No. 183,526, Sep. 2, 1980, abandoned.

[51] Int. Cl.³ .................................................. B01D 15/08
[52] U.S. Cl. ................................. 210/656; 210/198.2; 422/70
[58] Field of Search ............ 210/635, 656, 659, 198.2; 422/70

[56] References Cited

U.S. PATENT DOCUMENTS 3,463,615  8/1969  Sochor .
3,472,627  10/1969  Hadina ............................ 422/70 X
3,751,879  8/1973  Allington .
4,181,853  1/1980  Abu-Shumays .................... 210/656
4,233,030  11/1980  Twitchett ............................ 422/70
4,251,218  2/1981  Diggens ............................ 204/1 T

OTHER PUBLICATIONS

R. S. Deelder et al., "Post-Column Reactor Systems in Liquid Chromatography", J. of Chrom., 149 (1978) pp. 669–682.
CECl On-Line Column Eluate Concentrator, Bulletin I-118G 6/75, pp. 1-12.
Vance Nau et al., "Application of Microporous Membranes to Chemiluminescence Analysis", Anal. Chem., vol. 51, No. 3, Mar. 1979, pp. 424–428.
Introduction to Modern Liquid Chromatography by Snyder et al., 2nd edition, John Wiley & Sons, New York, pp. 740-746, 1979.

Primary Examiner—John Adee
Attorney, Agent, or Firm—Burke M. Halldorson

[57] ABSTRACT

Reagent is added to liquid chromatographic effluent to increase detection sensitivity of sample bands, or to enhance sensitivity with respect to interfering bands which overlap sample bands of interest, using one or more hollow fibers immersed within mobile reagent which is permeated through the walls of the fibers and, thus, ultimately diffused into the column effluent.

8 Claims, 3 Drawing Figures

LIQUID CHROMATOGRAPHIC METHOD AND POST-COLUMN EFFLUENT TREATMENT FOR DETECTION AND SEPARATION AT OPTIMIZED PH

This is a continuation of application Ser. No. 274,127, filed June 16, 1981, which is a continuation of application Ser. No. 183,526 filed Sept. 2, 1980, both abandoned.

FIELD OF THE INVENTION

The invention relates to the field of liquid chromatography and, more particularly, to an improved method and apparatus by which acid or base reagent is added to chromatographic column effluent to practice separation and detection at distinct and optimized pH conditions.

BACKGROUND OF THE INVENTION

The very significant potential of using post-column reactors to improve detection in modern liquid chromatography (HPLC) has long been recognized, but little applied. For example, in the publication by Gfeller et al., "Post-Column Derivatization in High-Performance Liquid Chromatography Using the Air Segmentation Principle: Application to Digitalis Glycosides," Journal of Chromatography 142 (1977), pp. 271-281, the authors state:

"Although the use of such reaction techniques after column chromatographic separation has been known for more than a decade with classical column techniques (e.g., amino acid analyzers), little has appeared in relation to modern HPLC. One reason is the many technical problems [ ] that still have to be solved."

Among specific difficulties that are described in the literature are problems directly involved with state of the the art post-column reactor designs. Thus, Snyder et al., "Introduction to Modern Liquid Chromatography", 2nd Ed. (1979), p. 740, state:

"The adaptation of reaction detection to modern LC columns requires careful attention to [] the design of equipment, because extra column effects can be serious. For these reasons reaction detectors have so far found rather limited use in modern LC."

Equivalent conclusions are also expressed by Frei et al., "Reaction Detectors in HPLC", Journal of Chromatographic Science, Vol. 17, March 1979, pp. 152-159, wherein the authors state: "the construction of proper reaction detectors comprises a constant struggle against band broadening." In still another recent publication by Jupille, "UV—Visible Absorption Derivatization in Liquid Chromatography", Journal of Chromatographic Science, Vol. 17, March, 1979, pp. 160-167, the author listed among disadvantages of the design or state of the reactors: "a need for hardware modification (with attendant loss in flexibility); and [ ] a risk of band broadening due to post-column mixing volume resulting in loss of resolution."

By way of further explanation, the often mentioned problem of avoiding band spreading is interrelated to various factors, among which is the mode for metering reagent. Any lack in consistency of metering produces fluctuations in reagent concentration in the effluent, which shows up as "noise" in the chromatograph developed by the detector.

The problem is especially severe where highly concentrated reagent is used, since minute fluctuations can produce high background "noise" levels that severely hamper the sensitivity of detection. While one of the choices of the prior art is to use concentrated reagent to avoid band spreading by sample dilution, the gain may, nevertheless, be offset at least partially by increased background noise levels.

Band spreading is also caused by diffusion of sample bands into one another as a function of time. Prior devices inherently appear to obtain poor reagent/effluent mixing, hence, extending the time factor. The deficiency is particularly shown by the description in the literature of reagent/effluent mixing devices as means for promoting faster reactions.

Prior solutions to these and other related problems can thus be said to often involve serious drawbacks, e.g., increased "noise", or may be equally as objectionable on the basis of adding too much complexity, e.g., air segmentation methods, to apparatus which has been characterized as already involving inherently disadvantageous "hardware modifications" and "attendant loss of flexibility".

An objective of the invention is accordingly to provide an improved liquid chromatographic method and apparatus characterized by the development of an improved post-column reactor for pH adjustment which requires little in the way of hardware modifications.

It is particularly an objective hereof to provide such improved method and apparatus which achieve essentially constant "pulseless" metering of acid or base reagent, and, in addition, significantly improved diffusion of the reagent into the chromatographic column effluent.

It is still a further objective hereof to provide such apparatus and method wherein sample dilution is minimized without need for resorting to the addition of highly concentrated forms of reagent as a means or requirement, or resorting to other objectionable process or apparatus restrictions.

Still a further objective hereof is to provide such method and apparatus, which in contrast with prior art methods and apparatus, are of significantly less cost to use and to maintain.

Terms

The term "hollow fiber membrane" means an extremely small tube or fiber having an internal diameter of between about 2-1,000 microns, and most preferably, about 50-500 microns, and which has the property to transport mobile reagent in permeation contact with the exterior wall portion of the fiber (or saturated within the fiber wall matrix), while rejecting from transport, at least a detectable amount of a sample species of interest, or a derivative proportional thereto, flowing as a component of liquid chromatographic effluent through the internal bore of the hollow fiber membrane.

"Reagent" means a chemical species or combination of species essentially the sole purpose of which, when introduced through the hollow fiber membrane into chromatographic column effluent, is to react chemically, directly or indirectly, with a sample species of interest or an interfering sample species less than perfectly resolved with respect to a sample species of interest, to produce measurable enhancement in the detection of said species of interest, or a monitored proportional derivative thereof, compared to the absence of the hollow fiber membrane/reagent combination.

"Mobile" refers to reagent in a state by which it may be permeated or transported through the wall or a wall portion of the hollow fiber membrane.

The Invention

The above-stated objectives of the invention are achieved by liquid chromatographic apparatus comprising a chromatographic column means, means to add sample to the chromatographic column means, means to add eluent to the chromatographic column means, whereby the sample is eluted through the chromatographic column means, and component species thereof appear in chromatographically displaced form in the effluent of the chromatographic column means, the improvement which comprises, a post-column reactor comprising a hollow fiber membrane through which the effluent of the chromatographic column means is fed to a liquid chromatographic detector, a pH modifying mobile reagent, said hollow fiber being in permeation contact with the mobile reagent for permeation transfer of the reagent into the effluent of the chromatographic column means.

A further aspect of the invention is the improved method of analyzing samples by liquid chromatography comprising adding sample to a chromatographic column means, adding eluent to the chromatographic column means effective to chromatographically displace species of the sample from the chromatographic column means, whereby chromatographically displaced sample species appear ultimately in the effluent of the chromatographic column means, the improvement which comprises, feeding the effluent of the chromatographic column means through the internal bore of a hollow fiber membrane, ultimately to a liquid chromatographic detector, and prior to detection, using the hollow fiber membrane for permeation transfer of a mobile reagent into the effluent of the chromatographic column means to enhance the sensitivity of detection of the method by effecting a pH change in the effluent.

An essential feature of the invention is the use of single or multiple hollow fiber membranes in conjunction with prior developed liquid chromatographic methods and apparatus. In the preferred device, multiple fibers are potted at each end into a tube sheet for purposes of isolating the inner portion or inner bore of the fibers and also to provide means for connecting the inner portion of the fibers to standard liquid chromatographic fittings. The center section of the hollow fiber "bundle", which may be coiled to conserve space, is immersed within mobile reagent. As such, the device is readily combined with standard and commercial forms of liquid chromatographic apparatus with minimal need for basic modification in the hardware.

Hollow fiber membranes useful in the practice of the invention are characterized by a molecularly porous wall structure obtained as an inherent property of the material used to make the fiber, or obtained as product of the manufacturing process, or a combination of both. The invention makes no claim, as such, to inventing the hollow fiber membrane structure per se. Typically used in practicing the method and apparatus of the invention are thus commercial hollow fiber membranes developed for other applications, and which are adaptable to the invention.

Among properties desired of the hollow fiber membrane, in addition to the ability to contain and transport reagent, and resist transport of at least part of the sample, is tolerance to contact with the various liquids to which the membrane is exposed. Particularly useful in this respect are porous cellulose membranes prepared such as by the method of U.S. Pat. No. 3,546,209. Such membranes may be either isotropic or anisotropic in structure. The transport properties of this type of membrane are produced typically by fabricating discretely sized pores piercing the fiber wall, e.g., by "pushing aside" the membrane material to form the pore structure. As such, the permeation characteristics are basically that of size selection and may be broadly applied to permeate widely diverse reagent species.

Synthetic polymeric membranes, such as produced typically from polyolefins and also silicone rubber, as well as a considerable group of other polymeric materials, may be adapted for use in the invention. Particularly useful are charged ion-exchange hollow fiber membranes produced by sulfonation or amination processes in order to obtain "Donnan exclusion" rejection properties of ionic species. Permeation through such membranes is often typically through a "tortuous" path defined in the molecular spaces between polymer molecules. The transport and selective properties of the solid matrix polymeric hollow fiber is thus often very specific and thus requires careful selection with reagent and sample in mind. Specific examples of this type of the membrane are detailed below with respect to some of the very important reagents.

The "leakage" characteristics of hollow fiber membranes used in the invention are oftentimes not highly critical. For example, leakage through the fiber wall of other than sample is often, if not inconsequential, not a phenomenon that will severely hamper the analysis. Thus, eluents used in the invention are generally characterized as noninterfering or substantially noninterfering. Reagent diluents, where used, may be selected for the same properties. Accordingly, leakage of these characterized components, assuming there is a net transfer one way or the other, may, at most, produce a dilution on the sample in the chromatographic effluent. Assuming a net loss of chromatographic effluent through any such transfer, a desirable concentration of the sample may in fact result from beneficial leakage phenomena producing higher detection sensitivity.

In addition, while it would be desired to have a hollow fiber membrane that rejected sample in the perfect sense, such is neither an absolute or essential requirement. While too much loss of sample can be consequential to the sensitivity of the analysis, substantial loss of sample does not necessarily mean severely detrimental results will occur. Thus, for illustrative example, 90 percent leakage of sample would not necessarily preclude highly sensitive analysis from being performed where the gain of sensitivity by the method is on the order of a thousandfold, which is not an unusual result possible with reagent addition methods. Since the amount of reagent necessary to achieve highly dramatic improvement in detection sensitivity can be very small, the selective transport properties of the membrane may in fact favor transport of the sample. That is, a greater leakage of sample than premeation of reagent may be experienced by use of a particular membrane, while at the same time obtaining enhancement in sensitivity of detection. Thus, selective transport properties of the hollow fiber membrane, favoring the reagent, is not an essential requirement of the invention in its broadest sense.

In respect to band spreading produced by dilution factors, or adding liquid volume to the chromatographic effluent, the invention has a very important advantage over prior art reagent addition methods. Thus, while it is contemplated that there is often a significant leakage of the nonactive component of the reagent into the chromatographic effluent, since other than perfect permselective qualities are present in hollow fibers, there is at the same time the mentioned ability of the fiber to extract fluid from the effluent, so that a net exchange of fluid volume is involved. For membranes which possess good sample rejection properties, it is thus possible to minimize dilution volume without resorting to difficult procedures that severely restrict the method.

In order to minimize band spreading due to geometry and flow pattern factors using the method and apparatus of the invention, it is desirable that if multiple hollow fibers be used, they each produce the same resistance to flow and, consequently, as the effluent stream is divided and flows in the multiple passages of the individual fibers, flow proceeds at a uniform rate. Thus, with flow dwell time in the individual fibers being substantially constant, tendency for band spreading is greatly reduced. This is typically achieved by using multiple fibers of the same internal diameter and length. Obviously, to overcome the effect entirely, fibers could be matched to produce exactly equivalent flow characteristics.

Also as a general rule, other considerations aside, the larger the fiber, the greater the tendency to produce band spreading by inherent fluid drag at the fiber wall/flow interface, hence producing an effect that if accentuated enough, or prolonged for long enough, can cause loss of resolution. The effect is minimized by using multiple fibers of extremely small diameters, and, which by means of larger surface area can pass reagent more quickly, frequently permitting the use of a shorter path of travel, and hence minimal band spreading based on diffusion of sample bands into one another as a factor of time. The rate of diffusion of the reagent in the chromatographic effluent is also effectively improved using small multiple hollow fiber membranes. Hence, very significant advantage in critical parameters is often achieved by the use of a post-column reactor design based on the use of multiple hollow fibers having satisfactory sample rejection properties, and connected in parallel between the chromatographic column means and detector.

Highly suited for use in the multiple fiber device are fibers of between about 100-300 microns in internal diameter for use in conventional bore liquid chromatography. In conjunction with microbore liquid chromatography such as described by Scott et al., *Journal of Chromatography*, Vol. 169, pg. 51 (1979) incorporated herein by reference, extremely small fibers in the range as low as the current manufacturing limit of about 20 microns I.D. would be usable. The wall thickness of the fibers is not always highly critical to rate of permeability as explained in U.S. Pat. No. 3,808,267, incorporated herein by reference. Generally, the wall thickness of fibers as used in the invention will be between about 5-250 microns. The length of the fibers can additionally vary depending on permeation and/or diffusion rates through the fiber wall. Generally, it is contemplated to use fibers of from about 10 centimeters to 200 centimeters in length, as a nonlimiting illustration. The restriction on length (and minimum I.D.) is ultimately a function of pressure drop through the fibers and back pressure on the fibers. Too much back pressure can rupture the fibers, thus limiting the pumping pressure. This can be compensated for, however, by equilibrating the pressure about the fibers with the internal pressure, such as by maintaining the fibers in a pressurized vessel. By taking the latter precautions, the length of the fibers may be increased to the point that resolution of the chromatographically displaced species is not too adversely affected.

The fibers or a portion thereof are in permeation contact with mobile reagent, the temperature, differential pressure with chromatographic effluent, and concentration of which significantly affect premeation rates in accordance with known membrane transfer phenomena. The reagent comprises, e.g., a pure liquid, pure gas or solution of reagent in a diluent or carrier whereby the reagent is mobile and may thus permeate the fiber wall. In some cases, an inert diluent such as methylene chloride is used which modifies the membrane such as by diffusion into the membrane to increase the rate of permeation of the reagent, also in accordance with known membrane phenomena. Other types of liquids, such as water or acetonitrile, are typically used as the reagent diluent.

In addition, it is also possible to use reagent, particularly ionic species, attached to active ion exchange sites of solutions or gels of ion-exchange resin, or agitated ion exchanged beads, in order to produce mobile reagent. This embodiment may be used, for example, with a charged ion-exchange hollow fiber membrane, whereby the reagent ion is exchanged with the exchangeable ion of the membrane and, thus, ultimately diffuses into the chromatographic column effluent. The embodiment is particularly useful wherever it would be desired that the ions similarly extracted from the chromatographic effluent, by the charged hollow fiber membrane, would be detrimental to detection. A means would thus be provided for minimizing return leakage. In addition, the embodiment can be used to prevent transfer of the relatively large polymeric counter ion of a given ionic reagent particularly where the counter ion would interfere or otherwise be detrimental to the analysis.

Two forms of reagent reservoirs or containers are particularly contemplated. The preferred form is generally described as a static reservoir, although the reagent may be agitated or stirred in order to prevent a concentration differential from occurring. Alternatively, a dynamic flow of the reagent, wherein continuously fresh reagent is pumped into contact with the fibers, may be used. The latter embodiment has advantages where contamination of the reservoir by leaking chromatographic effluent would be detrimental to the analysis. In such an embodiment, the fibers are placed, e.g., co-axially within a preferably flexible tube container to define an annular space between the fiber and inner wall of the tube. The fibers are potted at each end to isolate the inner bores of the fibers for connection to chromatographic fittings similarly as with respect to a static reservoir. Spaced tees are connected at the end of the tube container and reagent is continuously pumped into the annular space, most effectively in counter flow to the flow of the chromatographic effluent.

Because of less complexity, and typically very comparable performance to the dynamic reservoir embodiment, the static reservoir is to be preferred. Because the dilution of leaking sample into the relatively large reservoir of reagent produces an extremely dilute solution of a possible interfering species, the effect at most may be reflected as a slightly varying base line over a period of use. Ordinarily such would thus not justify the additional complexity associated with a dynamic reservoir embodiment.

The reaction kinetics of reagent addition methods, as well as prior developed reagents, are considered background technology to the invention and useful in its practice. Thus, the specific reagents and reactions developed for detection purposes and used in the invention are drawn from prior art sources. A fairly detailed listing of reactions considered suitable for use in post-column effluent reaction procedures is given by Snyder et al., supra, pages 740–746, herein incorporated by reference. Also incorporated by reference are the similar teachings of the prior cited references by Gfeller et al.; Frei et al.; and Jupille, together with a publication by Vance Nau et al., "Application of Microporous Membranes to Chemiluminescence", *Analytical Chemistry*, Vol. 51, No. 3, March 1979, pp. 424–428.

Favorable reaction condition necessary to promote the reaction must of course be present with this invention as with other reagent addition modes. Thus, reactions which require a major proportion of water in the final reaction mixture will generally require that aqueous eluents be used. The latter requirement is generally met with respect to ion-exchange and reverse-phase liquid chromatographic separation methods, or similar liquid chromatographic methods which employ an aqueous eluent or mobile phase in which the reagent is at least partially miscible. Similarly, for liquid chromatographic techniques such as normal phase chromatography, the invention is typically limited to the selection of reagents that can proceed in or require an organic solution in which the reagent is at least partially miscible. For slow reactions, elevated temperatures are imparted to the reaction mixture such as by means of a heated reaction delay loop which provides added residence time.

Liquid chromatographic detectors useful in the practice of the invention are particularly advantageously photometers, spectrophotometers and fluorometers used together with reagents which alter or produce light absorbance of sample species in the chromatographic effluent or which produce fluorescing derivative products. Among other liquid chromatographic detectors beneficially used in the mode of the invention are differential refractormeters, electrochemical detectors, radioactive detectors, and conductivity detectors, given for illustrative example only.

THE DRAWING

Yet further objects and advantages of the invention will, in part, be pointed out, and, in part, be apparent from the following detailed description taken together with the accompanying Drawing wherein.

DETAILED DESCRIPTION OF PREFERRED EMBODIMENTS

Figure 1:
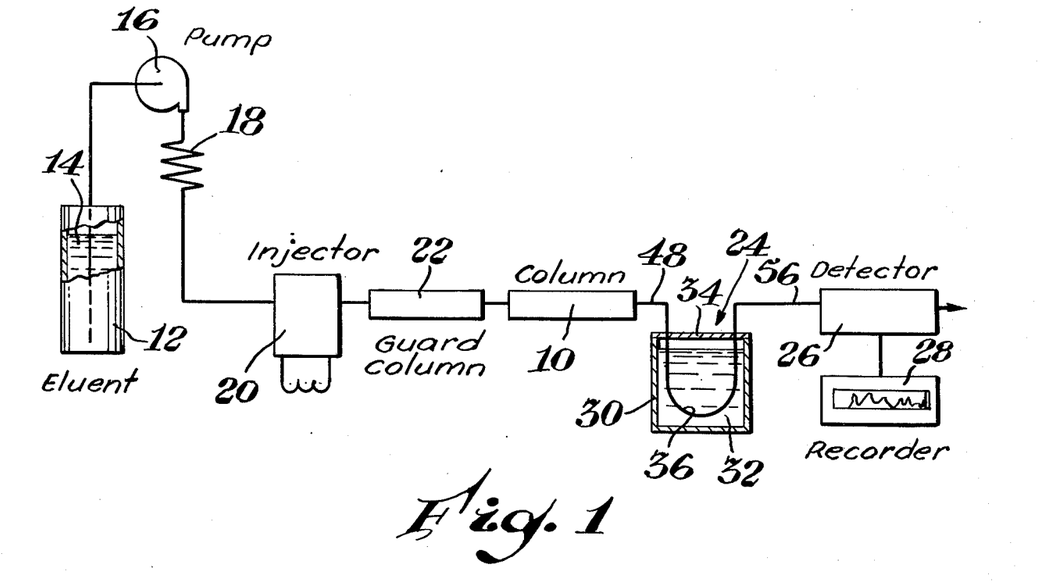
FIG. 1 is an elevational view of apparatus for performing liquid chromatography using post-column reagent addition in accordance with the principles and teachings of the present invention.

Referring to FIG. 1, there is shown a schematic view of liquid chromatographic apparatus which is desirably used in practicing the invention, and which comprises a chromatographic column or column means 10. The chromatographic column comprises a housed separating means typically in the form of a particulate packing or gel through which sample is eluted to separate the sample into component species. Diverse types of separating means may be used to construct a suitable chromatographic column, as described extensively, e.g., by Snyder et al., incorporated herein by reference.

Preferred means to add eluent or mobile phase to chromatographic column 10 comprises an eluent reservoir 12 containing eluent solution 14, the latter which is withdrawn from the reservoir by a chromatographic pump 16 equipped with an optional pulse damping coil 18.

Preferred means for adding sample comprise, e.g., a syringe loadable sample injection valve 20. Sample added to the system at valve 20 is swept through the apparatus by the pumped eluent solution through an optional guard column 22 to chromatographic column 10. The sample is eluted through column 10, and component species thereof thus ultimately appear chromatographically displaced in the chromatographic column effluent which is delivered to the reagent addition device or post-column reactor 24, described in further detail below.

The reagent addition device or reactor is optionally followed by a reaction delay coil or functionally equivalent element used whenever necessary to provide added reaction time vis-a-vis the species to be derivatized. Optionally, both or either the reagent solution or delay coil is maintained at a controlled temperature by suitable temperature control means, most simply, a temperature controlled plate which heats solution or fluid in which the delay coil is immersed; and/or which heats the reagent solution. The delay coil is ultimately followed by a detector 26 of a type suited for liquid chromatography.

In the detector, the effluent produces an electrical signal proportional to the property monitored such as light absorbance, fluorescence, etc., and which is directed from the detector ultimately to a suitable visual recorder 28 such as strip chart recorder, integrator, and the like, well-known to the art field.

Figure 2:
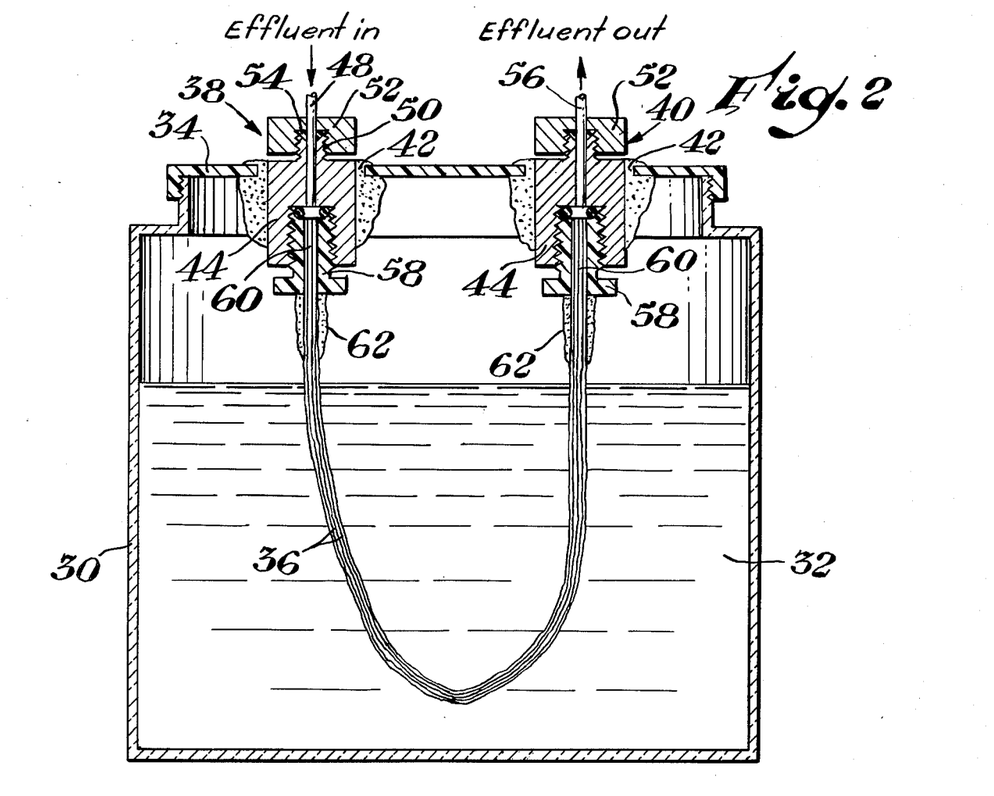
FIG. 2 is an enlarged cross-sectional view showing additional detail of the post-column reactor used in the FIG. 1 apparatus.

Referring to FIG. 2, a preferred form of reagent addition device, based on a simplicity factor, and acceptable performance for a great number of reagent addition reactions, is the design shown here. This is the "static" reservoir design which comprises basically a reservoir or reagent container or container means 30 preferably of glass or similarly inert material. Contained in the reservoir is mobile reagent 32. Reagent is periodically changed through a screw-cap or other suitable closure 34. Hollow fibers 36 are suspended in the reagent, between the points of an effluent in feed connection 38 and out feed connection 40. Each such connection is manufactured as follows: Openings 42 are drilled or otherwise formed in the cap, to which is attached a chromatographic adapter 44. The attachment is made by use of general purpose epoxy glue shown at 46. Chromatographic tubing 48 bringing chromatographic column effluent in is attached to the threaded nipple 50 of adapter 44, using a standard liquid chromatographic connecting nut and ferrule 52, 54. The out feed similarly connects to chromatographic tubing 56 leading to detector 28 through a similarly designated connecting nut 52 and ferrule 54.

A preferred form of fixing the fiber ends into the female part of adapter 44 is to mold a fitting 58 about the end portions 60 of the fibers. This fitting is made by using a RTV compound, e.g., Silastic brand mold making rubber J-RTV, to make a mold, using as the form for the mold, the commercial fitting which is to be duplicated. For an epoxy system, the fibers are threaded through the mold by drilling a small diameter hole for the threading purpose. The epoxy, e.g., Dow 331 Epoxy Resin/Ancamine LT Hardener, is poured into the mold and cured, with the fibers "wetted", or dry depending whether fiber swelling is expected in the end use application. After removal from the mold, the fiber ends are trimmed as required. A fiber coating layer 62, e.g., Silastic 730 RTV Fluorosilicone Sealant (from Dow Corning Corp.) is preferably applied in the area immediately adjacent the fitting to avoid fiber point stress, and thus minimize damage as may occur such as in the physical handling of the fibers.

The epoxy resin system is useful for aqueous reagent and eluent systems, certain aromatic solvents, and some hydrocarbons. For reagent solution or eluents which chemically attack epoxies, there is used in preference and for longer life, a Silastic Brand J-RTV material for constructing fitting 58 which otherwise is manufactured similar to the epoxy fitting. Fitting 58 is also suitably manufactured using a hollow commercial fitting through which the fibers are passed and which is filled with a RTV material, e.g., 730 RTV sealant, and the fill cured. The latter thus basically consists of the commercial chromatographic fitting with the ends of the fibers prepotted inside the hollow portion of the fitting by the in situ curing process using the described RTV material, or a substitute in situ curable substance.

Figure 3:
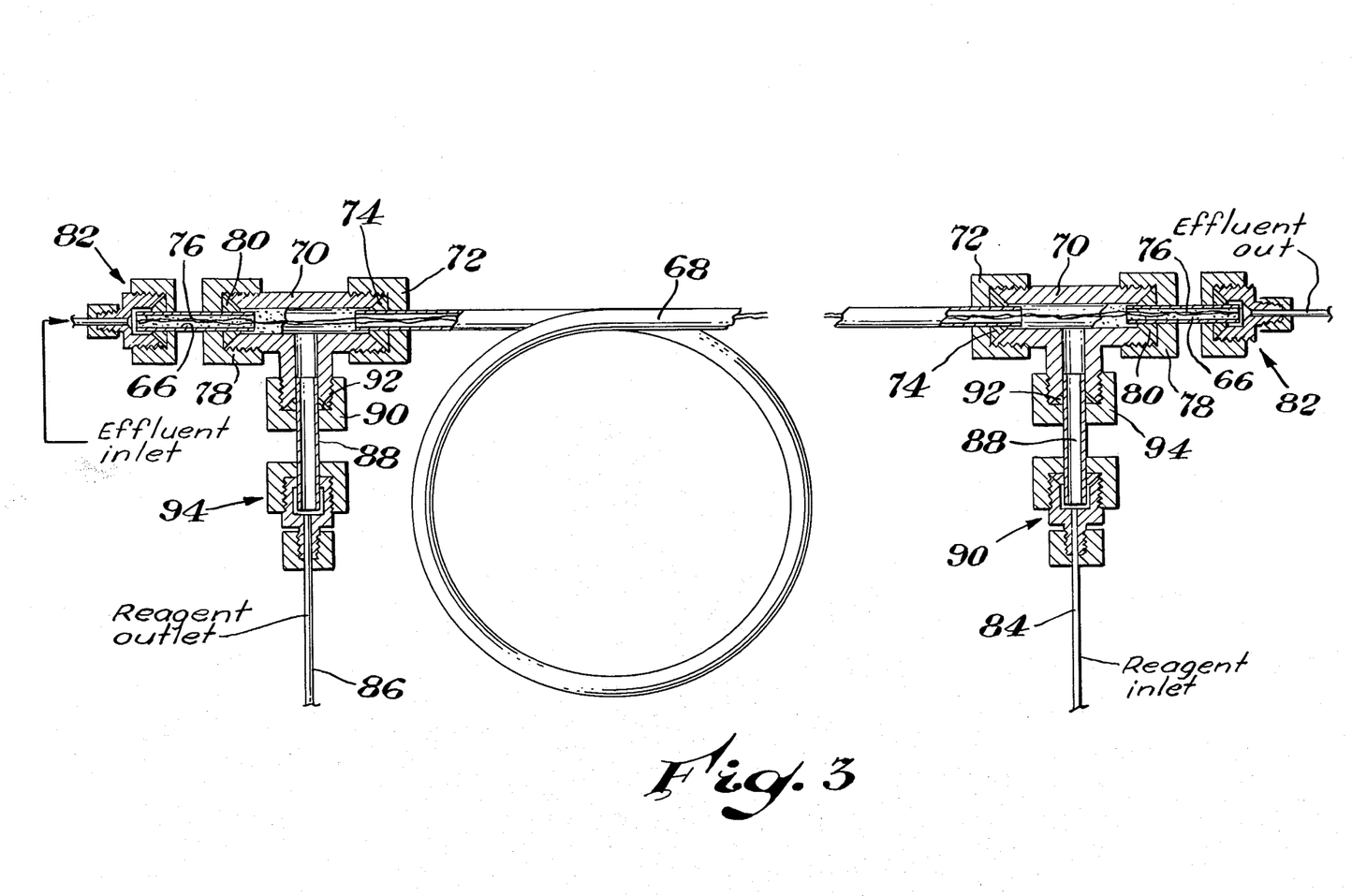
FIG. 3 is a view like FIG. 2 showing a modified form of the post-column reactor.

A preferred embodiment of the construction of a reagent addition device having the fibers immersed in counter flowing mobile reagent is illustrated in FIG. 3. This device is constructed of a center section of stainless steel tubing or tube container means or jacket means 68 through which a bundle of hollow fibers is inserted by suction or by gluing the end of a length of thread to a fiber bundle and pulling the fibers through the jacket means using water as the lubricant. A tee or tee fitting 70 is affixed to opposite ends, respectively, of the jacket means 68 using tube nuts 72 with ferrules 74 to make the attachment.

Exposed portions of the hollow fibers (outwardly of each tee) are dried and inserted into sealing tubes or tube elements 76, respectively, also preferably of stainless steel. A section of about six inches of fibers is left exposed between the sealing tube elements and tees 70 and the exposed fiber sections are coated with a suitable sealant, e.g., Silastic 732 RTV silicone rubber as indicated at areas 66, after which the sealing tubes are pushed down and coupled to the tees using tube nuts 78 and ferrules 80. Additional RTV sealant is injected into the sealing tubes using a blunt 20 gauge needle to completely fill each sealing tube but taking care not to force excess rubber into the tees. The RTV sealant is allowed to cure for 10 minutes to promote initial bonding and curing is completed with the fiber "wetted" or dry as the end-use application demands, and a razor blade used to cut the fiber bundle off flush with the end of the sealing tube. The device may then be coupled into the apparatus of FIG. 1, e.g., using reducing union assemblies 82, similarly is connected to a reservoir and pump means for supplying reagent, supplied through chromatographic tubing 84 and 86, respectively. These latter connections may be of the same type described, supra, using a tube element 88 joined at one end to tees 70 through tube nuts 90 and ferrules 92; and at the opposite end joined, respectively, to the reagent inlet and outlet 84, 86 through reducing union assemblies 94. The device as assembled defines contiguous flow channels comprising, respectively, the collective bores of the hollow fibers, and the spaces exterior of the fibers within jacket means 68 and which communicate, respectively, with chromatographic column 10 and the reagent supply source (not shown).

The described reagent addition devices operate by receiving the effluent of the chromatographic column which is thus routed internally through the hollow fibers. Simultaneously, solution containing mobile reagent (static or in the dynamic form) is contacted with the exterior surface of the hollow fibers, thus causing permeation of the reagent into the chromatographic effluent.

The invention is still further illustrated by reference to the specific teaching examples below.

EXAMPLE 1—HOLLOW FIBER MEMBRANES

Various hollow fiber membranes are used to construct reagent addition devices for use in the invention using the preferred static reservoir design. These include:

Device (A)

A device constructed of hollow fiber strands initially (prior to sulfonation) of 380 $\mu$O.D. and 300 $\mu$I.D., prepared by extrusion through a spinverette in the known manner. The fiber is formed of Product Code No. 4005 low density polyethylene, commercially available from The Dow Chemical Company. The fibers for purposes of sulfonation are wound on a glass mandrel (cage) and secured with Teflon tape. Since sulfonation weakens the fibers, it is desired that portions of the fibers where the fittings are to be attached are not subject to the sulfonating process. This is accomplished by looping discrete sections at a 90° angle to the circumferentially wound fiber sections to form a loop offset from the mandrel end. Using a Teflon cord attached to the loop, the fibers are suspended in a 3-neck/one liter flask equipped with a condenser and heating mandrel.

A sufficient volume of a 10% solution (v/v) of chlorosulfonic acid in methylene chloride is added to the flask to immerse the fibers (but not the looped end) and the solution is heated to reflux conditions (42° C.) and sulfonated for approximately 30 minutes. The fibers are retrieved and placed in methylene chloride and soaked for ½ hour followed by washing with deionized water. The loops are cut to provide unsulfonated ends for potting in fittings 58. Capacity is approximately 1 meg/gm. The device as constructed uses preferably 7 sulfonated fiber strands each 8 inches long.

Device (B)

A device constucted using 4 hollow fiber strands 8 inches long, 300 microns O.D., 230 microns I.D., obtained under the trade designation SR-$\alpha$/751–7010 from Bio-Rad Laboratories. The fibers are believed to comprise a copolymer of 40% $\alpha$-methylstyrene/60% polymethyl siloxane.

Device (C)

A device prepared using the basic sulfonation procedure and material of Device (A), supra, prepared using 16 fiber strands each 8 inches long, with a capacity of about 0.5 meg/gm, and final dimensions of approximately 375 micron O.D., 300 micron I.D.

Device (D)

Similar fibers to Device (A) are used in this device using 9 fiber strands, each about 10 inches long, sulfonated to achieve a capacity of about 0.7 meg/gm.

Device (E)

A device prepared from microporous cellulose hollow fibers, obtained commercially as a product of Spectrum Medical Industries, Inc., designated by Manufacturers Order No. 132272, and sold under the trademark SPECTRA/POR hollow fibre (HF) membrane. The device consists of 10 fiber strands, each 6 inches long, described as having a molecular weight cutoff in the range of 500–2000.

EXAMPLE 2—NITROPHENOL DETECTION

Separation of various nitrophenols using a silica based column, requires acid eluent pH conditions (about pH 6) for acceptable component resolution and/or for reason of column pH limitations. While the nitrophenols absorb at 280 nm, organic interferences in the sample matrix produce poor detection sensitivity.

This experiment illustrates an excellent solution to this analysis problem is available by producing a pH change through treating the chromatographic column effluent with $NH_3$ reagent, in order to produce derivative sample species which will absorb at a distinct wavelength that avoids matrix interferences. The experiment uses Device (A), and as the reagent, a solution of 30% ammonium hydroxide in water.

The experiment is conducted under the further conditions as follows: Aqueous eluent of 12 volume percent methanol, 0.08 M sodium perchlorate, 0.04 M ammonium acetate, adjusted to pH 6.1 with glacial acetic acid is pumped at 1.8 ml/min using a Milton Roy mini-pump through a Rheodyne 7120 sample injection valve with a 100 μl sample loop. The sample consisting of an identified organic matrix spiked with nitrophenols of interest is added to a Whatman Partisil Sax 10/25 chromatographic column, and detected using a LDC 1203 (Laboratory Data Control) photometer at 410 nm detection wavelength. A Spectro-Physics SP-4100 computing integrator is used for signal processing and computation.

Typical nitrophenols detectable by the system include 2,4,6-trinitrophenol, 2-sec butyl-4-6-dinitrophenol, 3-sec buty-2-hydroxy 5 nitrobenzene sulfonic acid and 3-sec butyl-4 hydroxy 5 nitrobenzene sulfonic acid. Detection limits for these compounds are at sub-ppm levels with no sample preparation. At this detection wavelength and pH change, the system is found to be very selective.

In a similar experiment to the above, 2,4,6-trinitrophenol species of interest is detected in admixture with co-eluting 2-sec-butyl-4,6-dinitrophenol, using as the reagent 2 M HCl in water. The chromatographic eluent is modified to a pH of about 2 (eluent pH 6.1). The pH adjustment selectively attenuates the dinitrophenol peak, to produce resolution and detection of the trinitrophenol species of interest in the sub-ppm range.

EXAMPLE 3—FLUORESCAMINE ADDITION

The fluorescamine reaction is a particularly important reagent addition reaction used, e.g., in the detection of primary amines. This experiment illustrates a specific example of the fluorescamine reaction as used in the mode of the invention.

The experiment is conducted using as the reagent additive device, Device (B), and as the reagent in which the fibers are immersed, a 2 mg/ml solution of fluorescamine in acetonitrile. A Varian 8500 chromatographic pump is used to pump 30 volume percent acetonitrile in water eluent solution containing 0.01 M ammonium acetate at 1 ml/min. A Rheodyne 7120 Injector (20 μl loop) is used to add a sample standard (1 ppm α-amino toluene in water) to a Waters μ-C-18 analytical HPLC column. The sample is detected using a duPont 836 fluorescence detector operated at 390 nm, 475 nm, excitation and emission wavelengths, respectively. A strong peak (offscale) is obtained at the ppm sample concentration level.

EXAMPLE 4—NINHYDRIN REACTION

The ninhydrin reaction is an excellent tool used in the detection, e.g., of amino acids, and is commonly utilized in commercial amino acid analyzers to develop blue color species derivatives which may be detected by a visible light photometer. The reaction can be beneficially utilized in the mode of the invention as illustrated in this Example.

Under the conditions of this experiment, eluent of 0.02 M citric acid in water adjusted to pH 4.0 with NaOH, is pumped by a Milton-Roy minipump at 0.52 ml/min through a Rheodyne 7120 injection valve equipped with a 200 μl loop where periodic injections of 50 ppm glycine are made to simulate peaks coming off of an analytical separation column. Device (C) is employed for the reagent addition purpose, using as the reagent, 100 ml of 10% ninhydrin solution in water. A hot plate is used to maintain the reagent at a temperature of 90° C.±5°. The ninhydrin treated solution is subsequently passed through a heated delay coil (2 meter, coiled Teflon tubing maintained at 90° C.) to provide a 3-minute delay for the reaction to occur. The reactor effluent is monitored using a Perkin-Elmer LC-55 UV/VIS absorption photometer operated at 600 nm. The peak of blue absorbance due to the ninhydrin-amino acid reaction product is recorded on a Sargent Welch Model SG Recorder. Excellent peaks are produced showing detection limits at the ppm level. Approximately 75% of the amino acid is estimated to have reacted under the conditions employed. No discoloration of the ninhydrin reagent solution is noted during the course of consecutive injections of sample.

EXAMPLE 5—IODIDE REACTION

Peroxides and other relatively strong oxidants will oxidize $I^-$ to $I_2$ to form highly colored $I_3^-$ in the presence of excess $I^-$. The reaction is useful, e.g., to determine the presence of peroxides or other strong oxidants in industrial process streams and products.

As an illustration of the use of this reaction in the inventive mode, eluent of 100 mg/liter $(NH_4)_2MoO_4$ in water, pH 5, is pumped at 1 ml/min into reagent additive Device (D), using as the reagent, stirred 1.0 M potassium iodide in water maintained at 54° C.+0.2° C. Repeated injections of aqueous hydrogen peroxide samples are made using a Rheodyne sample injection valve, 50 μl sample loop size (a separating column is not used in this experiment).

The sample is detected using a duPont 837 Visible UV photometer set at 375 nm. The recorded data is shown in the following Table.

TABLE

| Sample Size | Attenuation | Peak Height | Att'n × Peak |
|---|---|---|---|
| $H_2O_2$ | | | |
| 31.6 ppm | 32× | 208 | 6650 |
| 100 ppm | 128× | 126 | 16130 |
| 316 ppm | 256× | 108 | 27650 |
| 10 ppm | 32× | 70 | 2240 |
| 10 ppm | 16× | 139 | 2224 |
| 3.1 ppm | 16× | 49 | 784 |
| 3.1 ppm | 8× | 98.5 | 788 |
| 3.1 ppm | 4× | 197.5 | 790 |
| 1.0 ppm | 4× | 62.5 | 250 |
| 0.3 ppm | 4× | 19.5 | 78 |

The detection limit, calculated from the data, is estimated to be about 0.1 ppm. The method is considered to show linearity up to about 50 ppm hydrogen peroxide.

EXAMPLE 6—CELLULOSE FIBERS

The iodide reaction may similarly be applied to detect species e.g., $NO_2^-$, $ClO_3^-$, bleach and $Cl_2$. This example illustrates the detection of sodium nitrite, using the cellulose hollow fiber (Device (E), and using as the reagent, 0.1 N potassium iodide in water. In order to demonstrate the feasibility of the reactor-detector combination, sample standards of 100 to 1000 ppm, 20 μl sample injection size, are injected into pumped water eluent flowing at 1 ml/min, fed through Device (E), and the effluent of the Device monitored by a Perkin-Elmer LC-55 photometer set at 360 nm. Although not considered optimized, excellent detector sensitivity response is achieved, producing an estimated detection sensitivity comparable to that of hydrogen peroxide in the preceding example.

What is claimed is:

1. Liquid chromatographic apparatus comprising a silica based chromatographic column means, means to add sample to the chromatographic column means, a reservoir of eluent of a pH nondetrimental to the silica chromatographic column means, a chromatographic pump means to add the eluent to the chromatographic column means, whereby the sample is eluted through the chromatographic column means, and component species thereof appear in chromatographically displaced form in the effluent of the chromatographic column means, the improvement which comprises a post-column reactor comprising a hollow fiber membrane through which the effluent of the chromatographic column means is fed to a liquid chromatographic detector, a pH modifying mobile reagent, said hollow fiber being in permeation contact with the mobile reagent for permeation transfer of the reagent into the effluent of the chromatographic column means.

2. The apparatus of claim 1 wherein said post-column reactor comprises multiple hollow fiber membranes.

3. The apparatus of claim 1 comprising a reservoir means containing acid or base mobile reagent, wherein the reservoir means is of a type noncontinuously replenished by reagent.

4. The apparatus of claim 1 comprising a photometer as the detector.

5. Method of analyzing samples by liquid chromatography comprising adding sample to a silica based chromatographic column means, adding eluent to the chromatographic column means effective to chromatographically displace species of the sample from the chromatographic column means, whereby chromatographically displaced sample species appear ultimately in the effluent of the chromatographic column means, the eluent being at a pH in the range nondetrimental to the silica chromatographic column means, the improvement which comprises feeding the effluent of the chromatographic column means through the internal bore of a hollow fiber membrane, ultimately to a liquid chromatographic detector, and prior to detection, using the hollow fiber membrane for permeation transfer of a mobile reagent into the effluent of the chromatographic column means to enhance the sensitivity of detection of the method by effecting a pH change in the effluent.

6. The method of claim 5 using multiple hollow fiber membranes connected between the chromatographic column means and detector and immersed within mobile reagent.

7. The method of claim 5 wherein said mobile reagent is contained within a noncontinuously replenished reservoir.

8. The method of claim 5 wherein the sample comprises nitrophenols.

* * * * *

UNITED STATES PATENT AND TRADEMARK OFFICE
CERTIFICATE OF CORRECTION

PATENT NO. : 4,451,374

DATED : May 29, 1984

INVENTOR(S) : Dennis P. Peterson et al.

It is certified that error appears in the above—identified patent and that said Letters Patent is hereby corrected as shown below:

Col. 1, line 40, delete the word "the" second instance.

Col. 1, line 44, delete "[]" and insert --[ ]--.

Col. 2, line 51, delete "2-1,000" and insert --20-1,000--.

Col. 3, line 17, delete the comma "," after "comprises".

Col. 4, line 62, delete "premeation" and insert --permeation--.

Col. 6, line 14, delete "premeation" and insert --permeation--.

Col. 7, line 22, delete "condition" and insert --conditions--.

Col. 7, line 50, delete "refractormeters" and insert --refractometers--.

UNITED STATES PATENT AND TRADEMARK OFFICE
CERTIFICATE OF CORRECTION

PATENT NO. : 4,451,374

DATED : May 29, 1984

INVENTOR(S) : Dennis P. Peterson et al.

It is certified that error appears in the above—identified patent and that said Letters Patent is hereby corrected as shown below:

Col. 10, line 2, add the word --and-- before the word "similarly".

Col. 10, line 36, delete "spinverette" and insert --spinnerette--.

Col. 10, line 59, delete "meg/gm" and insert --meq/gm--.

Col. 10, line 63, delete "constucted" and insert --constructed--.

Col. 11, line 4, delete "meg/gm" and insert --meq/gm--.

Col. 11, line 12, delete "meg/gm" and insert --meq/gm--.

Col. 11, line 55, delete "buty-2-hydroxy" and insert --butyl-2-hydroxy--.

Signed and Sealed this

Eighteenth Day of December 1984

[SEAL]

Attest:

Attesting Officer

GERALD J. MOSSINGHOFF

Commissioner of Patents and Trademarks